United States Patent [19]
Frantz et al.

[11] Patent Number: 5,794,627
[45] Date of Patent: Aug. 18, 1998

[54] DISPOSABLE MANDIBULAR ADVANCEMENT APPLIANCE

[76] Inventors: Don E. Frantz, 400 Medical Center Blvd. #209, Webster, Tex. 77598; Michael D Frantz, 1019 E. Foster, Couer d'Alene, Id. 83814

[21] Appl. No.: 766,651

[22] Filed: Dec. 16, 1996

Related U.S. Application Data

[63] Continuation-in-part of Ser. No. 493,926, Jun. 23, 1995.

[51] Int. Cl.$^6$ .......................................... A61F 5/56
[52] U.S. Cl. ............... 128/848; 128/859; 433/6; 602/902
[58] Field of Search .......... 128/848, 859–862; 2/2; 602/902; 433/6

[56] References Cited

U.S. PATENT DOCUMENTS

| | | | |
|---|---|---|---|
| Re. 33,442 | 11/1990 | George | 128/860 |
| D. 302,036 | 7/1989 | George | D24/34 |
| 3,536,069 | 10/1970 | Gores | 128/861 |
| 4,169,473 | 10/1979 | Samelson | 128/136 |
| 4,304,227 | 12/1981 | Samelson | 128/136 |
| 4,305,709 | 12/1981 | Bruhn | 128/861 |
| 4,376,628 | 3/1983 | Aardse | 128/861 |
| 4,505,672 | 3/1985 | Kurz | 433/6 |
| 4,715,368 | 12/1987 | George | 128/136 |
| 4,825,881 | 5/1989 | Bessler | 128/859 |
| 4,901,737 | 2/1990 | Toone | 128/848 |
| 4,986,283 | 1/1991 | Tepper | 128/859 |
| 5,003,994 | 4/1991 | Cook | 128/848 |
| 5,018,533 | 5/1991 | Hawkins | 128/848 |
| 5,046,512 | 9/1991 | Murchie | 128/848 |
| 5,082,007 | 1/1992 | Adell | 128/860 |
| 5,092,346 | 3/1992 | Hays | 128/848 |
| 5,117,816 | 6/1992 | Shapiro | 128/200.24 |
| 5,195,890 | 3/1993 | Johansson | 433/172 |
| 5,203,324 | 4/1993 | Kinkade | 128/201.11 |
| 5,267,862 | 12/1993 | Parker | 433/215 |
| 5,277,202 | 1/1994 | Hays | 128/848 |
| 5,313,960 | 5/1994 | Tomasi | 128/848 |
| 5,316,020 | 5/1994 | Truffer | 128/848 |
| 5,365,945 | 11/1994 | Halstrom | 128/848 |
| 5,409,017 | 4/1995 | Lowe | 128/848 |
| 5,499,633 | 3/1996 | Fenton | 128/848 |

OTHER PUBLICATIONS

Young, Terry, et al., The Occurence of Sleep–Disordered Breathing Among Middle Aged Adults, *The New England Journal of Medicine* (Apr. 29, 1993), vol. 328, No. 17, pp. 1230–1235.

Isono, Shiroh, et al., "Anatomy and Physiology of Upper Airway Obstruction" in *Principles and Practice of Sleep Medicine*, 2nd Edition, W.B. Saunders Company (1994), pp. 642–656.

(List continued on next page.)

*Primary Examiner*—Michael A. Brown
*Attorney, Agent, or Firm*—Vaden, Eickenroht & Thompson, L.L.P.

[57] ABSTRACT

A mandibular advancement, or positioning, device for short-term or one-time use is described. The appliance has an upper tray and a lower tray holding impression material, into which the patient bites. The impression material, and optional adhesive, serve as a way to secure the trays to the patient's upper and lower teeth, and, therefore, to the patient's maxilla and mandible. Preferably, the front portions of the trays are bendable or flexible, for allowing the use of just a few sizes of trays for all patients. A connector is attached to a rear area of the lower tray and adjustably connects to the upper tray at or near the center of the upper tray front area, so that the connector easily may be manually pulled forward and temporarily locked in place to advance the mandible. The device may also include spacers or bite planes for opening the patient's bite. The device is particularly useful for short-term use in applications which do not require long-term comfort and durability, such as sleep-lab testing of the usefulness of mandibular advancement in treating a particular patient, or as a step in surgical anesthesia to enlarge a patient's pharyngeal airway space.

15 Claims, 3 Drawing Sheets

OTHER PUBLICATIONS

Browman, Carl, et al., "Obstructive Sleep Apnea and Body Weight" in *Chest* (Mar., 1984), pp. 435–436.

Schmidt–Nowara, Wolfgang, et al., "Oral Appliances for the Treatment of Snoring and Obstructive Sleep Apnea: A Review" in *Sleep*, No. 6, vol. 18 (1995), pp. 501–510.

Lowe, Alan, "Dental Appliances for the Treatment of Snoring and Obstructive Sleep Apnea" in *Principles and Practice of Sleep Medicine*, 2nd Edition, W.B. Saunders Company (1994), pp. 722–735.

Clark, Glenn, et al., "The Effect of Anterior Mandibular Positioning on Obstructive Sleep Apnea", *Am.Rev.Respir. .Dis.*, vol. 147 (1993), pp.624–629.

W. Cassel, "Sleep Apnea and Personality", in *Sleep*, vol. 16, No. 8, (1993), pp. S56–S57.

Willy Chua et al., "Obstructive Sleep Apnea", in *Postgraduate Medicine*, Sleep Apnea, vol. 95/No. 2 (Feb. 1, 1994).

Glenn T. Clark, et al., "Effect of Anterior Mandibular Positioning on Obstructive Sleep Apnea", *A, Rev Res or Dos Vp*; 147, pp. 624–629 (1993).

Dr. George Cook, D.D.S., "Snoring and Sleep Apnea Questions/Answers * A New Treatment Device", Compiled and Written by The Holdingford Dental Clinic (1990).

Scott E. Eveloff et al., "Efficacy of a Herbst mandibular Advancement Device in Obstructive Sleep Apnea", *Am J Respir Crit Care Med* vol. 149. pp. 905–909 (1994).

Peter T. George, D.D.S., "Treatment of Snoring and Obstructive Sleep Apnea with a Dental Device", *General Denistry*, pp. 294–298 (Aug. 1993).

Dr. Harry W. Tepper, "The Tepper Oral Proprioceptive Stimulator *, An Innovative Appliance Developed by Dr. Harry W. Tepper for the Treatment of Sleep Apnea and Chronic Snoring", Great Lakes Orthodonics, Ltd.

David R. Hillman, "Sleep Apnea and Myocardial Infarction", *Sleep*, vol. 16, No. 8, pp. S23–S24 (1993).

Poul Jennum, et al., "Cognitive Function and Snoring", *Sleep*, vol. 16, No. 8, pp. S62–S64 (1993).

Alan A. Lowe, "Can We Predict the Success of Dental Appliance Therapy for the Treatment of Obstructive Sleep Apnea Based on Anatomic Considerations!", *Sleep*, vol. 16, No. 8, pp. S93–S94 (1993).

H. Edward Lyon, D.D.S., "Treatment of Snoring and Obstructive Sleep Apnea", *Compend Contin Educ Dent*, vo. XIII, No. 5, pp. 416–420.

Robyn A. O'Sullivan et al, "Mandibular Advancement Splint: The Effects on Snoring and Obstructive Sleep Apnea", *Sleep*, vol. 16, No. 8, pp. S143 (1993).

Karen E. Shelton, et al., Adipose Tissue Deposition in Sleep Apnea, *Sleep*, vol. 16, No. 8, pp. S103 and S95 (1993).

Cohen, Robert B., DMD, "Obstructive Sleep Apnea: A Mandibular Positioning Device for Treatment and Diagnosis of an Obstruction Site", *Compendium*, vol. 16, No. 6 pp.619–627 (Jun., 1995).

DISPOSABLE MANDIBULAR ADVANCEMENT APPLIANCE

This application is a continuation-in-part of prior, co-pending application, "Elastic Mandibular Advancement Appliance", Ser. No. 08/493,926, filed Jun. 23,1995, by applicants Michael D. Frantz and Don E. Frantz, D.D.S.

BACKGROUND OF THE INVENTION

1. Field of the Invention.

This invention relates generally to oral appliances for controlling the position of the human mandible to effect the size of the pharyngeal airway. More specifically, this invention relates to a removable mandibular advancement appliance which pulls the jaw forward and opens the bite vertically. The invention may be used for preventing snoring and obstructive sleep apnea (OSA), for testing the efficacy of such an appliance on snoring or OSA patients, or for keeping the airway open during anesthesia or other situations in which there is a risk of obstruction of the airway due to the position or state of the user. A preferred embodiment of the invention is a disposable appliance that can be conveniently, quickly, and safely used in sleep labs and surgical settings without custom-building the appliance for the individual patient.

2. Related Art.

It is well documented in the literature that an oral appliance that opens the bite and moves the mandible forward will greatly reduce sleep apnea and snoring. It is believed that such appliances work by opening the airway for greater airflow, by moving the mandible and/or tongue forward to increase the pharyngeal airway space.

Pending U.S. patent application, "Elastic Mandibular Advancement Appliance", Ser. No. 08/493,926, filed Jun. 23, 1995, ("Frantz '926") is herein incorporated by reference. In Frantz '926, applicants Don E. Frantz, D.D.S. and Michael D. Frantz disclose a totally adjustable, removable, oral appliance for long-term use as a treatment for snoring and/or OSA. The Frantz '926 mandibular advancement, or positioning, device uses elastic bands to pull the jaw forward and removable bite planes to open the bite.

The Frantz '926 appliance has an upper plastic base shaped to conform to the patient's maxillary dentition (upper teeth), soft tissues and hard palate. Also, the appliance has a lower plastic base shaped to conform to the patient's mandibular dentition (lower teeth), and soft tissues. The lower plastic base has a set of removable posterior occlusal bite planes. The upper surface of the bite planes occlude, that is, come together, with the lower surface of the upper plastic base to open the bite. Different sets of bite planes have slightly different thicknesses, for providing different vertical openings of the mouth from about 8–14 mm to optimize the effect of the appliance. The upper plastic base has a set of outwardly-extending plastic retention hooks, one on the right and one on the left anterior buccal portion. The lower plastic base also has a set of outwardly-extending retention hooks, one on the right and one on the left of the posterior buccal portion. Specially-formed elastic urethane bands, or standard orthodontic elastics, are attached to both the upper and lower retention hooks to pull the mandible forward. Each set of urethane bands may have a slightly different length and different modules of elasticity, for providing different advancement amounts to further optimize the effect of the appliance.

An important object of the Frantz '926 appliance is to provide a custom-fit appliance with high patient acceptance, comfort, and treatment success for a long period of use. The Frantz '926 appliance is preferably custom-molded to fit the patient's dentition, and the elastic bands and bite planes are preferably custom-fit to optimize the effectiveness of the appliance for each patient. The custom-fitting techniques involve an initial office visit, significant lab work, and at least one follow-up office visit. Due to the elasticity of the bands, the Frantz '926 appliance will not cause the temporomandibular joint problems or unwanted tooth movement or soreness that a rigid appliance would tend to cause after long-term use. If the patient's condition or needs change during long-term use of the appliance, the elastic bands and removable bite planes can be changed to affect both the amount of forward movement of the lower jaw and the amount of vertical bite opening.

What is still needed, however, is a disposable appliance which is effective for short-term use without custom construction or adjustment. A disposable appliance is needed for testing of snoring or sleep apnea patents and for use by anesthesiologists and other medical practitioners needing short-term mandibular advancement. These needs are satisfied by the present invention.

SUMMARY OF THE INVENTION

An object of the present invention is to provide effective, convenient, quick, safe, and reliable mandibular advancement for situations in which the advancement, and the resulting opening of the airway, is needed for shorter periods of time, for example, during several hours of surgery or over-night in a sleep lab. The appliance of the present invention is effective without requiring custom-fitting or expensive lab work, so that the invention may be economically used and disposed of after one use. The present invention is particularly effective as a disposable, economical testing or "titration" device to help medical professionals determine whether a mandibular advancement appliance alleviates the patient's snoring or OSA problems, and whether the added investment in a custom-built appliance would be beneficial. The present invention is also particularly effective as a disposable device for one-time use by anesthesiologists, to prevent a patient's airway from becoming obstructed by the patient's own tongue while under anaesthesia.

Both installation and removal of the invented appliance are quick and straightforward, allowing quick action in preparation for surgery or testing or during an emergency in surgery. The appliance of the present invention comprises two trays, an upper tray for temporary securement to the user's maxillary dentition, and a lower tray for temporary securement to the patient's mandibular dentition. The appliance also comprises a connection means for connecting the upper and lower trays in a position which pulls the lower tray, and therefore, the mandible, forward relative to the upper tray and the maxilla. Minimal adjustment is needed to obtain an effective advancement of the mandible, and that advancement may be done by a quick movement of preferably a single connector.

The trays are preferably of the general type that may be referred to as bite trays, for holding an impression material, such as silicone putty like Kerr's Citricon TM into which the patient bites. The putty hardens enough against the teeth and gums, and particularly into the undercut areas of the generally bell-shaped teeth, so that the putty acts as the securement means to hold the upper and lower trays in place on the maxillary and the mandibular dentition, respectively, during the testing or surgery. Preferably, bite planes or other spacers extend from either the upper tray or the lower tray, to occlude against the opposite tray to open the bite.

The connection means is preferably engaged, as soon as the securement of the trays to the dentition is accomplished, to pull the mandible forward. The connection means is preferably incrementally adjustable, so that the medical professional may choose one of several "settings" for the connection means, and therefore, one of several amounts of mandibular advancement. The connection may be elastic, however, the preferred connector is generally non-elastic, to prevent significant stretching of the connector by the patient and the consequent backward movement of the mandible that might obscure the testing results or allow the mandible and tongue to fall backward during surgery. Thus, the preferred connection means provides the testing professional or anesthesiologist an adjustable but exact, repeatable and known amount of advancement for the short-term use of the appliance. Precision and repeatability are normally a high priority for these short-term uses, rather than comfort and patient acceptance, which are priorities for long-term applications.

The connection means of the present invention is also preferably a quickly connectable, and quickly removable or releasable connector. Preferably, the connector comprises a single connector or fastener with a single handle for extending out the front of the patient's mouth for easy access. In this way, the technician or anesthesiologist can quickly install and incrementally adjust the connector for use, and can quickly disconnect the connector in an emergency.

Typically, during sleep-lab testing or surgery, the connector will be adjusted several times. In the sleep-lab, the technician will typically start the testing with the connector in a relatively posterior (rearward) position, that is, pulling the lower tray forward little or none to get a reference point for the patient's response. The technician will then incrementally adjust the connector and lower tray forward to monitor the patient's response. In a surgical application, an anesthesiologist will typically first adjust the connector and lower tray to a relatively anterior (forward) position to ensure the mandible and tongue is advanced during the crucial early stages of anesthesia. During the surgery, the anesthesiologist may release the connector or lock it in a relatively rearward (non-advanced) position. After surgery, the anesthesiologist again may advance the connector and lower tray in preparation for the patient's coming out of anesthesia.

Most adult patient's can be quickly fitted into one of three standard sizes of upper and lower trays. The trays are preferably adapted to flex slightly during the insertion and/or biting steps, to enhance the fit of the standard sizes to the particular size and shape of the patients mouth. Alternatively, the trays may be rigid and therefore offered in a wide variety of sizes to fit many different mouth sizes and shapes.

Once the short-term use of the present invention is over, the connection means may be disconnected and the trays pulled off of the dentition for removal of the appliance from the patient's mouth. The appliance may then be discarded without great loss of investment in time and equipment.

DESCRIPTION OF THE PREFERRED EMBODIMENTS

Figure 1:
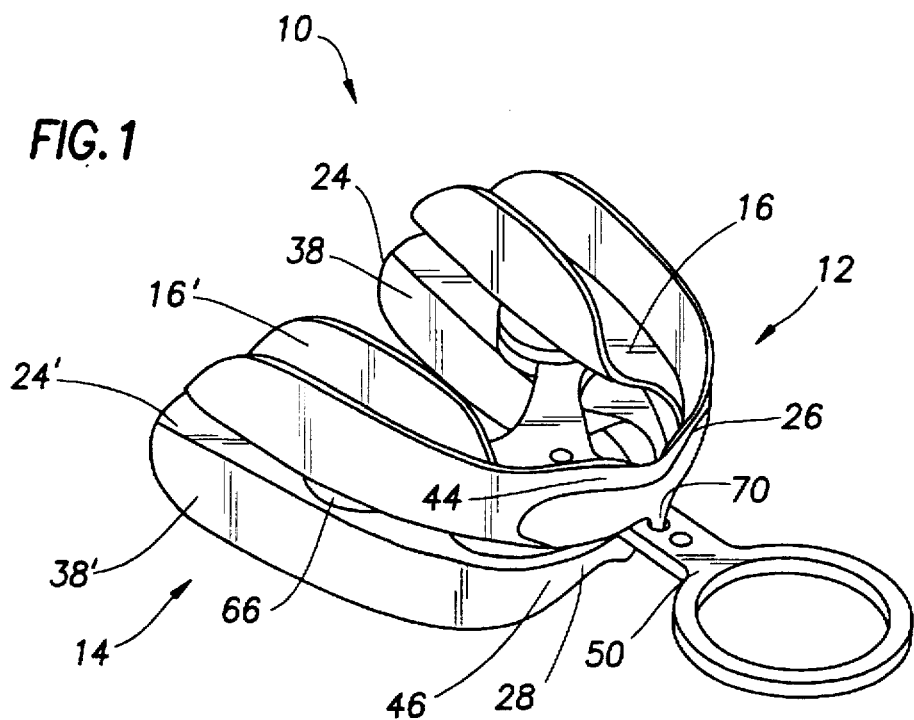
FIG. 1 is a perspective view of the one embodiment of the invention, showing upper and lower trays and a connector, but with the lower tray not yet pulled forward.

Referring to FIGS. 1–6, there is shown one, but not the only, embodiment of the invented mandibular advancement appliance 10. Depicted in FIG. 1 are upper tray 12 and lower tray 14, without impression putty, but arranged generally as they would be in a patient's mouth before advancement of the lower tray 14 and the mandible. In this description and in the claims, portions of the appliance 10 described as "anterior", "front", or "forward" refer to areas or directions generally near or toward the anterior teeth (front six teeth). The terms "posterior", "rear", or "rearward" refer to areas or directions generally near or toward the posterior teeth (back from the front six teeth).

Figure 3:
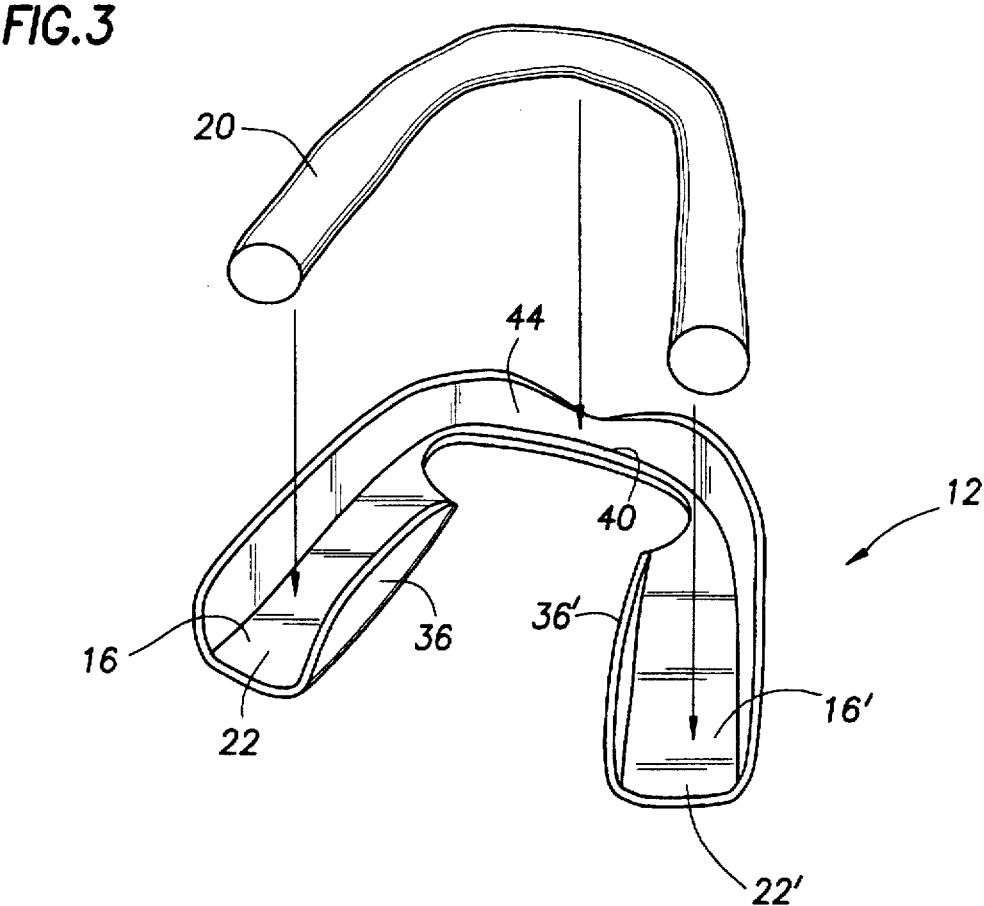
FIGS. 3 is a detail perspective view of an embodiment of a securement means for holding the tray on the patient's teeth and soft tissues, that is, impression putty for being received in an upper tray for being bitten into by the upper teeth of a patient.
Figure 4:
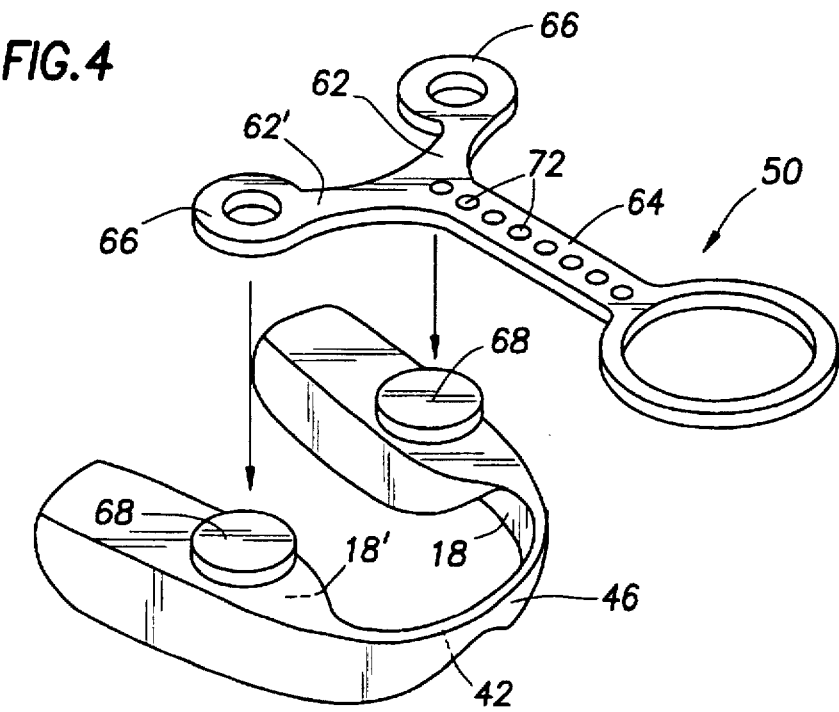
FIG. 4 is a perspective view of the lower tray and connector of the embodiment of FIG. 1 and 2, showing button spacers onto which the connector is attached.

The trays 12, 14 are generally U-shaped, and each has an anterior portion (hereafter, also called "front portion 26, 28") and left and right side posterior portions (hereafter, also called side portions 36, 36', 38, 38'). The left and right side posterior portions have side troughs 16,16', 18,18', and the anterior portions have smaller front troughs 40, 42. Into the troughs are placed ropes of putty 20 (as shown in FIG. 3), such as silicone putty, a vinyl polysiloxane impression material, or other impression material, such as may be known now in the dental arts or others developed in the future. The putty 20 preferably extends all the way from the tray left ends 22, 24, around the front portions 26, 28, and to the tray right ends 22', 24'. Upon placement of the putty-filled trays 12, 14 into the patient's mouth, the patient's teeth (not shown) extend into the troughs 16, 16', 18, 18', 40, 42, and the patient is instructed or caused to bite into the putty 20 in the troughs. The putty 20 moves around the slightly bellshaped teeth to extend into the teeth undercuts, and hardens around the teeth and against the soft tissues, in order to secure the trays 12, 14 onto the upper and lower teeth and tissues.

The tray front portions 26, 28 are preferably designed to be flexible to an extent that allows each tray to flex near the front portions 26, 28 to conform more accurately to the particular patient's mouth. While it is anticipated that about three standard adult sizes and about three standard pediatric sizes will fit most patients, the additional feature of tray flexing at the tray front 26, 28 helps fit in-between-size or unusually-shaped mouths. To achieve this flexibility, the preferred tray front portions 26, 28 are narrower or flatter than their side portions 36, 36', 38, 38'. That is, the front trough 40, 42 widths are small relative to the side troughs, for holding the putty 20 for the front teeth while not interfering with flexibility of the front walls 44, 46. Thus, the side troughs 16, 16', 18, 18' are wide enough from side wall to side wall to receive the patient's molars, while the front troughs 40, 42 may be just wide enough from side wall to side wall to hold the putty into which bite the front teeth.

An alternative embodiment comprises upper and lower trays with non-flexible, rigid anterior (front) portions. With such an embodiment, the medical professional would be supplied with a large assortment of trays, giving him/her the choice of a wide variety of tray sizes.

An alternative, less preferred embodiment, eliminates the front troughs 40, 42. In such an embodiment, the side troughs and putty comprise the securement means.

Figure 2:
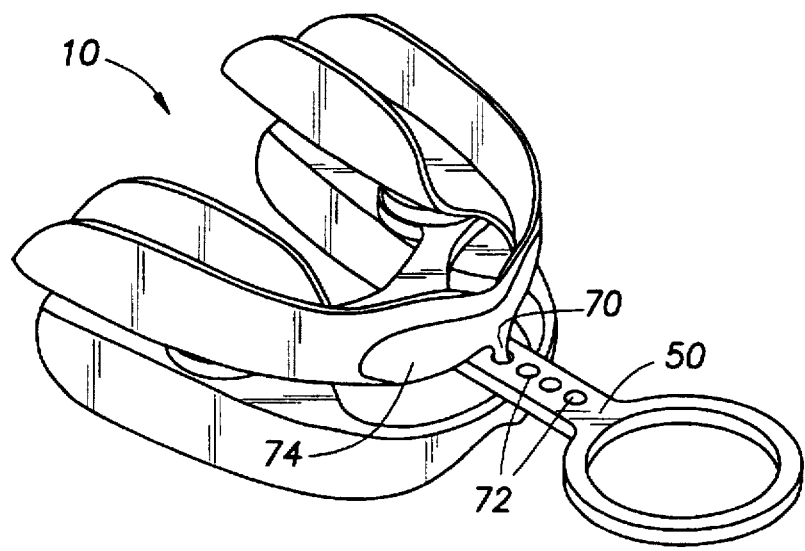
FIG. 2 is a perspective view of the embodiment of FIG. 1, showing the lower tray pulled forward and the connector engaged to the upper tray.
Figure 5B:
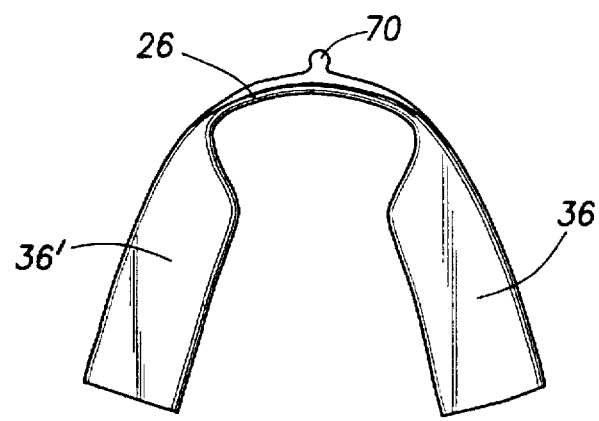
FIG. 5B is a bottom view of the upper tray of the embodiment of FIGS. 1 and 2, shown without the connector of FIG. 5A attached to the upper tray.
Figure 5A:
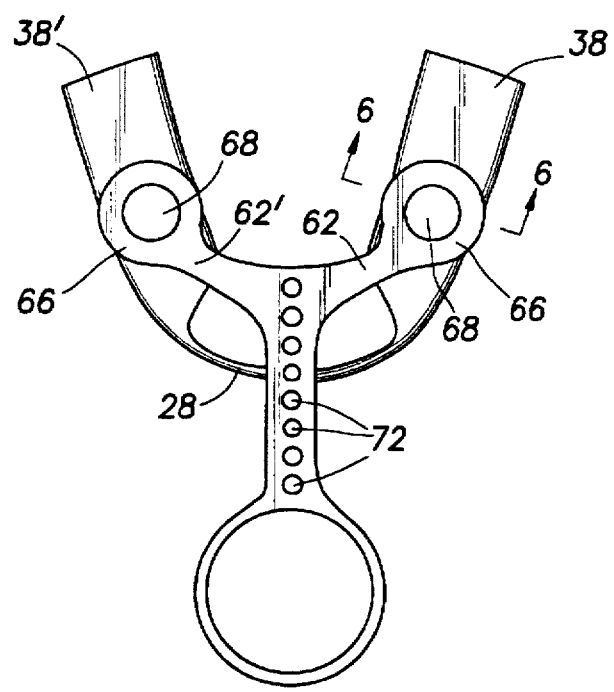
FIG. 5A is a top view of the lower tray and connector of the embodiment of FIGS. 1 and 2.
Figure 6:
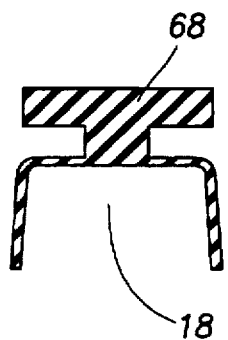
FIG. 6 is a cross-sectional view of the lower tray of FIG. 5A, along the line 6–6 in FIG. 5A, showing the button without the pull-strap attached.

FIGS. 1,2, 4 and 5A show a connection means that is a single "pull-strap" connector, for pulling and locking the lower tray in a forward position. The pull-strap 50 is generally a Y-shape, with two wings 62, 62' for connection to the lower tray 14 and a handle 64 for connection to the upper tray 12 and for extending forward out of the patient's mouth. The wings 62, 62' each have a ring 66 with a hole for snapping around the buttons 68 located on the left and right upper surfaces of the lower tray 14 about midway along the tray side portions 38, 38'. A pin 70 or other protrusion extends from the front portion 26 of the upper tray 12 to engage in the plurality of holes 72 in the handle 64. As shown in FIG. 5A, the line of holes 72 generally corresponds to incremental adjustments in advancement of the lower tray 14 and the mandible forward relative to the upper tray 12 and the maxilla. By snapping the pull-strap handle 64 up to receive the pin 70, typically in one of the more rearward of the holes 72, the lower tray 14 is locked in place anterior relative to the upper tray 12, until the pull-strap 50 is snapped down off of the pin 70. As shown in FIG. 2, when the pull-strap 50 is pulled forward to the more rearward of the holes 72, the front portion 28 of the lower tray can be seen to be significantly forward of the front portion 26 of the upper tray.

In addition to serving as attachment points for the pull-strap 50, the buttons 68 serve as spacers or bite planes to separate the trays 12, 14 during use, and therefore, to open the bite of the patient. As discussed above, this further contributes to the opening of the airway of the patient.

In use, the technician or anesthesiologist selects a small, medium, or large tray size for the patient. He/she places a rope of putty 20 in both the upper and lower trays. Optionally, he may first spray an adhesive into the tray to further attach the putty to the trays beyond the degree that the putty will naturally stick to the tray due to its inherent adhesiveness. The lower tray 14 has been previously fitted with a pull-strap 50, by snapping or pushing the rings 66 down around the buttons 68. Both trays are then inserted into the patient's mouth, and the patient bites down into the putty. After sufficient time for the putty to adequately set up, typically about a minute, the pull-strap 50 is pulled forward and locked on the upper tray pin 70 at a position desired by the technician or anesthesiologist. This position may be adjusted as desired to increase or decrease the amount of advancement.

Optionally, the appliance may be pre-fitted to the patient by a nurse or technician several minutes or hours before the testing or surgery, removed from the patient after the putty has hardened, and then reinserted just prior to testing or surgery. For this reinsertion, the medical professional may also apply a spray-on adhesive on the surface of the hardened putty before reinsertion into the patient's mouth, to further enhance the securement of the putty to the teeth.

Various putty materials and methods of handling the putty may be used, but the preferred embodiment comprises improved putty packaging and methods of handling. Silicone putty is provided in a single-use amount and packaged in a single flexible pouch along with a vial or capsule of accelerator. In this embodiment, the user obtains the single pouch, releases the accelerator by breaking open the vial by a quick snap of the vial through the material of the pouch, kneads the accelerator into the putty to get thorough mixing. The user then cuts or zips open the pouch and squeezes out the putty to form two ropes for the trays.

The invented appliance 10 may be made by various methods, preferably by injection molding of plastic such as acrylic or PETG. The Pin 70 may be a protrusion extending integrally from the molded material, or, alternatively, may be part of a separate piece 74 bonded onto the front wall 44 of the upper tray, for example. The pull-strap 50 may be made of thick urethane, for example, to make the pull-strap 50 resilient enough to snap onto and off of the buttons 68 and the pin 70, but not elastic enough to allow significant stretching of the pull-strap by the patient during use.

Optionally, all interior surfaces of the trays may be texturized. All trough interior surfaces and surfaces that may be contacted by the impression material may be texturized to better bond with the impression material.

Alternatively, other connection means may be used to lock the lower tray to the upper tray in an advanced position. For example, a cord may connect to the lower tray on both buccal sides of the lower tray and may extend up to attach to a forward protrusion of the upper tray by hooking into one of several notches in a surface of the forward protrusion. Other connection means may include a plurality of fasteners and may include fasteners that range from elastic to rigid, but the described preferred connection means is very effective because of its simplicity and ease of use, and because it does not stretch to create an unknown amount of advancement. The described preferred connection means is also easy to use because it consists of only a single part that attaches easily to both sides of the lower tray to pull the lower tray forward uniformly. The preferred connection means is controlled by a single handle from outside the patient's mouth and with a single action of the hand. Preferably, but not necessarily, the single connector handle extends at least one inch forward from the front portion of the upper tray, even when the connector is adjusted to its rearmost position, for easy access by the medical professional.

The buttons 68 are preferably an integral part of the lower tray, rather than being removable and changeable. Optionally, the pull-strap 50 may be integral with the lower tray, and need not be removed from the lower tray for the short-term use of the invention. Alternatively, the buttons may be attached to the tray by some method that would not pose the risk of the buttons tearing off during use.

Although this invention has been described above with reference to particular means, materials and embodiments, it is to be understood that the invention is not limited to these disclosed particulars, but extends instead to all equivalents within the scope of the following claims.

We claim:

1. An oral appliance for use in advancing a patient's lower jaw, comprising:

upper and lower, generally "u" shaped bite trays each including troughs along both sides and the front portions and adapted to fit over the upper and lower teeth of the patient, the upper tray having fastening means near its front portion, a supply of material which, when applied to the troughs of each tray, is adapted to adhere thereto, and, when the trays are fitted over the teeth, form an impression which adheres to the teeth to the extent necessary to be temporarily retained in the patient's mouth, and connecting means having an inner end connected to the lower tray rearwardly of the fastening means when the trays are in place and of such length that its outer end extends forwardly of the patient's lips, and means intermediate its inner and outer ends which is releasably fastenable to the fastening means of the upper tray, said connecting means being sufficiently elastic that its outer end may be manipulated to permit it to be fastened to the upper tray in different forward and rearward positions, or, with the connecting means releasably fastened to the lower tray prior to installation of the trays, the lower tray will, when installed, force the lower tray and thus the lower jaw to a desired forward position with respect to the upper tray, but nevertheless being sufficiently non-elastic as to prevent substantial movement of the lower tray from the position in which it is releasably fastened, said trays and said impressions, upon hardening, being sufficiently elastic that they may be removed from the teeth.

2. As in claim 1, wherein the inner end of the connecting means is releasably connected to the lower tray.

3. As in claim 1 or 2, wherein each side of one tray has a bite plane engageable with the bite surfaces on the other tray.

4. As in claim 3, wherein the bite planes are on the lower tray.

5. As in claim 4, wherein each bite plane is formed on the means releasably attaching the inner end of the connecting means to the lower tray.

6. As in claim 1, wherein the inner end of the connecting means has wings each connected to an opposite side of the tray.

7. As in claim 6, wherein each wing is releasably connected to a side of the tray by a hole in one tightly fittable over a button on the other.

8. As in claim 1 or 2, wherein the means for releasably fastening the inner end of the connecting means to the front position of each tray comprises a pin on one and a series of spaced holes on the other fittably closely over the pin.

9. As in claim 8, wherein the pin is on the front portion of the upper tray, and the holes are formed in the outer end of the connecting means.

10. As in claim 1, wherein each tray is of such construction that its sides may flex inwardly and outwardly to accommodate different sized jaws.

11. As in claim 10, wherein the supply of impression material is prepackaged for storage and supply along with the trays and connecting means, and includes components which, when combined, are adapted to be formed into a moldable shape for application to the troughs.

12. As in claim 1, including means on the trays for enhancing the adherence of the impressions material to the troughs.

13. As in claim 1, wherein the impression material is of such consistency as to flow and harden in the undercut areas of the teeth.

14. A method of advancing a patient's lower jaw, with the use of an oral appliance which includes upper and lower, generally "u" shaped bite trays each including troughs along both sides and the front portion thereof and adapted to fit over the upper and lower teeth of the patient, the upper tray having fastening means near its forward portion, a supply of impression material, and connecting means having an inner end connected to the lower tray rearwardly of the fastening means when the trays are in place, and means intermediate its inner and outer ends which is releasably fastenable to the fastening means of the upper tray, so that its outer end extends beyond the front portion of the lower tray, the steps of applying the impression material to the troughs of each tray so as to cause it to adhere thereto, fitting the troughs of the upper and lower trays to the upper and lower teeth including their undercut portions to form an impression of the teeth, manipulating the outer end of the connecting means so as to locate the fastening means thereon in a position to releasably engage the fastening means on the upper tray, fastening the connecting means to the upper tray when so located, and pulling the outer end of the connecting means to unfasten it from the upper tray and thereafter manipulating the upper end of the connecting means to refasten it, and refastening the connecting means to the upper tray in another position, or, if desired, enabling the appliance to be removed by lifting the trays from the teeth.

15. A method of advancing a patient's lower jaw, with the use of an oral appliance which includes upper and lower, generally "u" shaped bite trays each including troughs along both sides and the front portion thereof and adapted to fit over the upper and lower teeth of the patient, the upper tray having fastening means near its forward portion, supply of impression material, and connecting means having an inner end connected to the lower tray rearwardly of the fastening means when the trays are in place, and means intermediate its inner and outer ends which is releasably fastenable to the fastening means on the upper tray, so that its outer end will extend beyond the front potion of the lower tray, the steps of applying the impression material to the troughs of each tray so as to cause it to adhere thereto, fitting the troughs of the upper and lower trays to the upper and lower teeth to form an impression of the teeth, removing the trays from the patient's teeth, manipulating the outer end of the connecting means so as to locate the fastening means thereon in a position to releasably engage the fastening means on the upper tray, fastening the connecting means to the upper tray when so located, and by fitting the upper and lower trays and impressions over the upper and lower teeth so as to advance the lower teeth with the lower tray a distance corresponding to the advance of the lower tray, and thereafter manipulating the outer end of the connecting means to release its fastening means from that of the upper tray so that the connecting means may be refastened to the upper tray in another position, or, if desired, permit the appliance to be removed by lifting the trays from the teeth.

* * * * *

UNITED STATES PATENT AND TRADEMARK OFFICE
CERTIFICATE OF CORRECTION

PATENT NO. : 5,794,627
DATED : August 18, 1998
INVENTOR(S) : Frantz, et al

It is certified that error appears in the above-identified patent and that said Letters Patent is hereby corrected as shown below:

On the title page, under item [56], insert the following references:

```
U.S. Patent No. 3,224,442
U.S. Patent No. 4,413,978
U.S. Patent No. 5,562,106
U.S. Patent No. 5,570,704
```

Signed and Sealed this

Twenty-ninth Day of February, 2000

Attest:

Attesting Officer

Q. TODD DICKINSON

Commissioner of Patents and Trademarks